US00PP27550P3

(12) United States Plant Patent
Wood

(10) Patent No.: US PP27,550 P3
(45) Date of Patent: Jan. 17, 2017

(54) ***DIERVILLA* PLANT NAMED 'SMNDRSF'**

(50) Latin Name: *Diervilla rivularis*
Varietal Denomination: SMNDRSF

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 59 days.

(21) Appl. No.: 14/545,151

(22) Filed: Mar. 31, 2015

(65) Prior Publication Data

US 2016/0295761 P1 Oct. 6, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Diervilla* plant named 'SMNDRSF', characterized by its upright and outwardly spreading plant habit; vigorous growth habit and rapid growth rate; freely branching habit; dense and bushy appearance; leaves are dark burgundy in color in the spring and become dark red in color in the autumn; and good garden performance.

2 Drawing Sheets

Botanical designation: *Diervilla rivularis.*
Cultivar denomination: 'SMNDRSF'.

BACKGROUND OF THE INVENTION

The present invention relates to a new and distinct cultivar of *Diervilla* plant, botanically known as *Diervilla rivularis*, commonly referred to as bush honeysuckle and hereinafter referred to by the cultivar name 'SMNDRSF'.

The new *Diervilla* is a product of a planned breeding program conducted by the Inventor in Grand Haven, Mich. The objective of the breeding program was to develop new freely branching *Diervilla* plants with dark leaf color.

The new *Diervilla* plant originated from a self-pollination in June, 2008 of *Diervilla rivularis* 'Troja Black', not patented. The new *Diervilla* plant was discovered and selected by the Inventor in May, 2011 as a single plant within the progeny of the stated self-pollination in a controlled environment in Grand Haven, Mich.

Asexual reproduction of the new *Diervilla* plant by softwood cuttings in a controlled greenhouse environment in Grand Haven, Mich. since June, 2011 has shown that the unique features of this new *Diervilla* plant are stable and reproduced true to type in successive generations of asexual reproduction.

SUMMARY OF THE INVENTION

Plants of the new *Diervilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNDRSF'. These characteristics in combination distinguish 'SMNDRSF' as a new and distinct *Diervilla* plant:

1. Upright and outwardly spreading plant habit.
2. Vigorous growth habit and rapid growth rate.
3. Freely branching habit; dense and bushy appearance.
4. Leaves are dark burgundy in color in the spring and become dark red in color in the autumn.
5. Good garden performance.

Plants of the new *Diervilla* can be compared to plants of the parent, 'Troja Black'. In side-by-side comparisons, plants of the new *Diervilla* differ primarily from plants of 'Troja Black' in leaf color as leaves of 'Troja Black' are green tinged with brown in color in the spring becoming red (lighter in color than leaves of plants of the new *Diervilla*) in the autumn.

Plants of the new *Diervilla* can be compared to plants of *Diervilla rivularis* 'Summer Stars', not patented. In side-by-side comparisons, plants of the new *Diervilla* differ primarily from plants of 'Summer Stars' in leaf color as leaves of 'Summer Stars' are green slightly tinged with red in color in the spring becoming orange red in the autumn.

BRIEF DESCRIPTION OF THE PHOTOGRAPHS

The accompanying colored photographs illustrate the overall appearance of the new *Diervilla* plant showing the colors as true as it is reasonably possible to obtain in colored reproductions of this type. Colors in the photographs may differ slightly from the color values cited in the detailed botanical description which accurately describe the colors of the new *Diervilla* plant.

The photograph on the first sheet is a side perspective view of a typical plant of 'SMNDRSF' grown during the autumn.

The photograph on the second sheet is a close-up view of a typical plant of 'SMNDRSF' grown during the spring.

DETAILED BOTANICAL DESCRIPTION

The aforementioned photographs and following observations, measurements and values describe plants grown in the early summer in three-gallon containers in a polypropylene-covered shadehouse in Grand Haven, Mich. and under cultural practices typical of commercial *Diervilla* production. During the production of the plants, day temperatures ranged from 18° C. to 27° C. and night temperatures ranged from 5° C. to 10° C. Plants were two years old when the photographs and the description were taken. In the description, color references are made to The Royal Horticultural Society Colour Chart, 1995 Edition, except where general terms of ordinary dictionary significance are used.

Botanical classification: *Diervilla rivularis* 'SMNDRSF'.

Parentage: Self-pollination of *Diervilla rivularis* 'Troja Black', not patented.

Propagation:

*Type*.—By softwood cuttings.

*Time to initiate roots, summer*.—About four weeks at temperatures about 23° C.

*Root description*.—Medium in thickness; whitish in color.

*Rooting habit*.—Moderate branching; medium density.

Plant description:

*Plant form and growth habit*.—Perennial deciduous shrub; upright and outwardly spreading plant habit, mounding; vigorous growth habit and rapid growth rate.

*Branching habit*.—Freely branching habit; about 17 primary lateral branches develop per plant; pinching enhances lateral branch development.

*Plant height*.—About 40 cm.

*Plant diameter* (*area of spread*).—About 70 cm.

Lateral branch description:

*Length*.—About 42 cm.

*Diameter*.—About 4 mm.

*Internode length*.—About 5 cm to 5.5 cm.

*Aspect*.—Erect to outwardly.

*Strength*.—Strong.

*Texture*.—Slightly pubescent on youngest stems; mostly smooth, glabrous.

*Color, upper surface*.—Close to 60A; striations, close to 59A.

*Color, lower surface*.—Close to 165A and 165B.

Leaf description:

*Arrangement*.—Opposite, simple.

*Length*.—About 13.5 cm.

*Width*.—About 5.6 cm.

*Shape*.—Lanceolate to ovate.

*Apex*.—Acuminate.

*Base*.—Obtuse.

*Margin*.—Serrulate.

*Texture, upper and lower surfaces*.—Smooth, glabrous.

*Venation pattern*.—Pinnate.

*Color*.—Developing leaves, during spring, upper surface: Close to 144A overlain with close to 60A. Developing leaves, during the spring, lower surface: Close to 146D overlain with close to 60A. Fully expanded leaves, during the summer, upper surface: Close to 146A and 147A overlain with close to 59A; venation, close to 146A and 147A. Fully expanded leaves, during the summer, lower surface: Close to 146B; towards the margins, close to 59B; venation, close to 146B. Fully expanded leaves, during the autumn, upper surface: Close to 185A fading to close to 60A; slight stippling, close to 187A; venation, close to 185A and 60A. Fully expanded leaves, during the autumn, lower surface: Close to 146D; towards the margins, close to 59B; venation, close to 146D.

*Petioles*.—Length: About 6 mm. Diameter: About 2 mm. Texture, upper surface: Slightly pubescent. Texture, lower surface: Smooth, glabrous. Color, upper surface: Close to 148A slightly tinged with close to 183D. Color, lower surface: Close to 144A.

Flower description:

*Flower appearance and arrangement*.—Salverform flowers arranged in terminal cymes; freely flowering habit with about 25 flowers per inflorescence; flowers face upright to outwardly.

*Fragrance*.—None detected.

*Natural flowering season*.—Plants flower continuously during the late spring to mid-summer in Michigan; flowers not persistent.

*Flower diameter*.—About 1.5 cm.

*Flower length*.—About 2 cm.

*Flower throat diameter* (*at base of petal lobes*).—About 3 mm.

*Flower tube length*.—About 9 mm.

*Flower tube diameter* (*at base of tube*).—About 1.5 mm.

*Inflorescence diameter*.—About 4 cm.

*Inflorescence height*.—About 3.5 cm.

*Flower buds*.—Length: About 1 cm. Diameter: About 3 mm. Shape: Oblong. Color: Close to 144B.

*Petals*.—Quantity and arrangement: Five fused with apices free. Length: About 5 mm. Width: About 3 mm. Shape: Narrowly oblong. Apex: Obtuse. Margin: Entire, undulate. Texture, upper and lower surfaces: Slightly pubescent; velvety. Color: When opening and fully opened, upper surface: Close to 150A; flower throat, close to 154D. When opening and fully opened, lower surface: Close to 149B; flower tube, close to 154D.

*Sepals*.—Quantity and arrangement: Five in a single whorl. Length: About 2 mm. Width: About 0.5 mm. Shape: Narrowly deltoid. Apex: Acuminate. Margin: Entire. Texture, upper and lower surfaces: Smooth, glabrous. Color, upper surface: Close to 59B. Color, lower surface: Close to 145A.

*Peduncles*.—Length: About 3 mm. Diameter: About 1 mm. Aspect: Erect to about 45° from vertical. Strength: Strong. Texture: Smooth, glabrous. Color, upper surface: Close to 59A. Color, lower surface: Close to 145A.

*Pedicels*.—Length: About 8 mm. Diameter: About 1 mm. Aspect: About 25° from peduncle axis. Strength: Strong. Texture: Slightly pubescent. Color, upper surface: Close to 184A. Color, lower surface: Close to 145C.

*Reproductive organs*.—Stamens: Quantity per flower: Five. Filament length: About 5 mm. Filament color: Close to 145D. Anther length: About 3 mm. Anther shape: Lanceolate. Anther color: Close to 17A. Pollen amount: None observed. Pistils: Quantity per flower: One. Pistil length: About 1.4 cm. Stigma shape: Round. Stigma color: Close to 144B. Style length: About 1.4 cm. Style color: Close to 144B. Ovary color: Close to 144B.

*Fruits and seeds*.—Fruit and seed development have not been observed on plants of the new *Diervilla*.

Garden performance: Plants of the new *Diervilla* have been observed to have good garden performance and to tolerate rain, wind and temperatures ranging from −27° C. to 35° C.

Pathogen & pest resistance: Plants of the new *Diervilla* have not been shown to be resistant to pathogens and pests common to *Diervilla* plants.

It is claimed:

1. A new and distinct *Diervilla* plant named 'SMNDRSF' as illustrated and described.

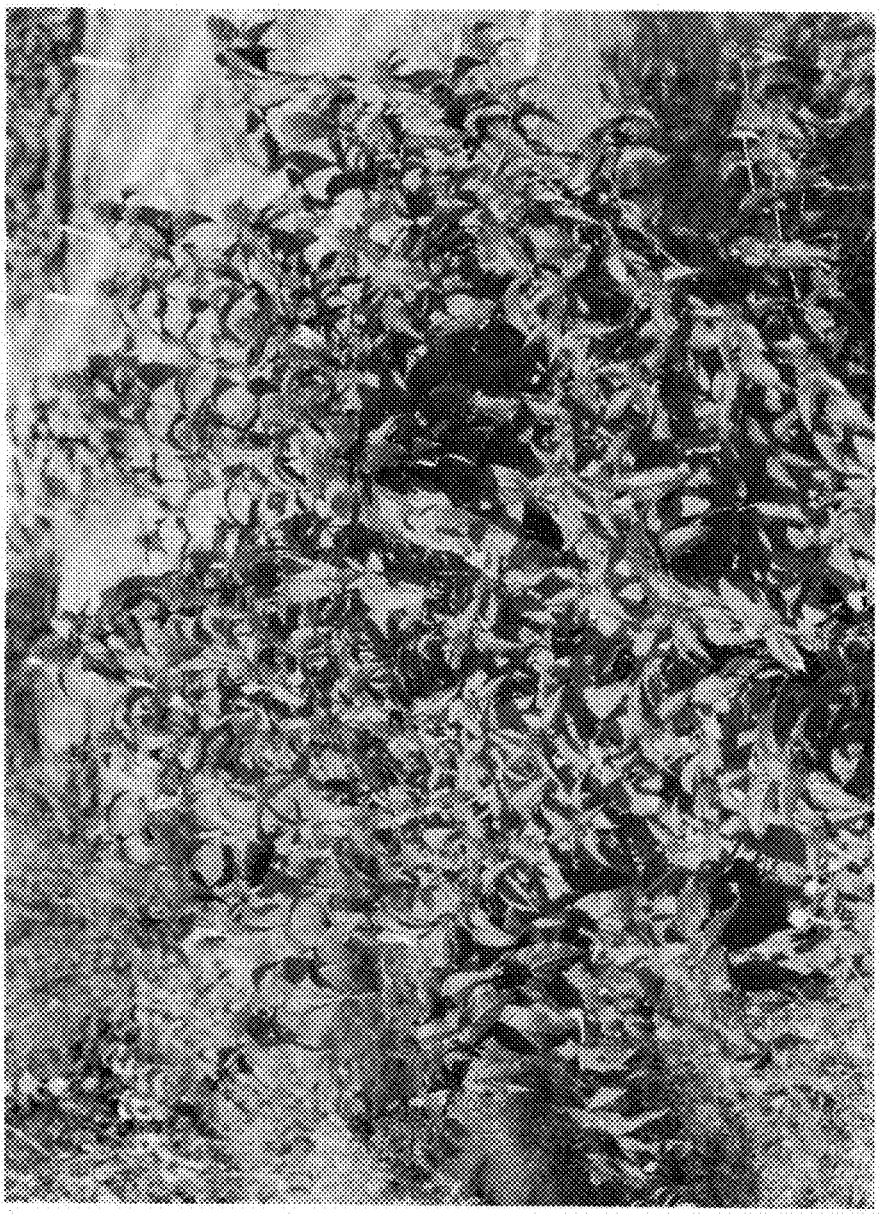

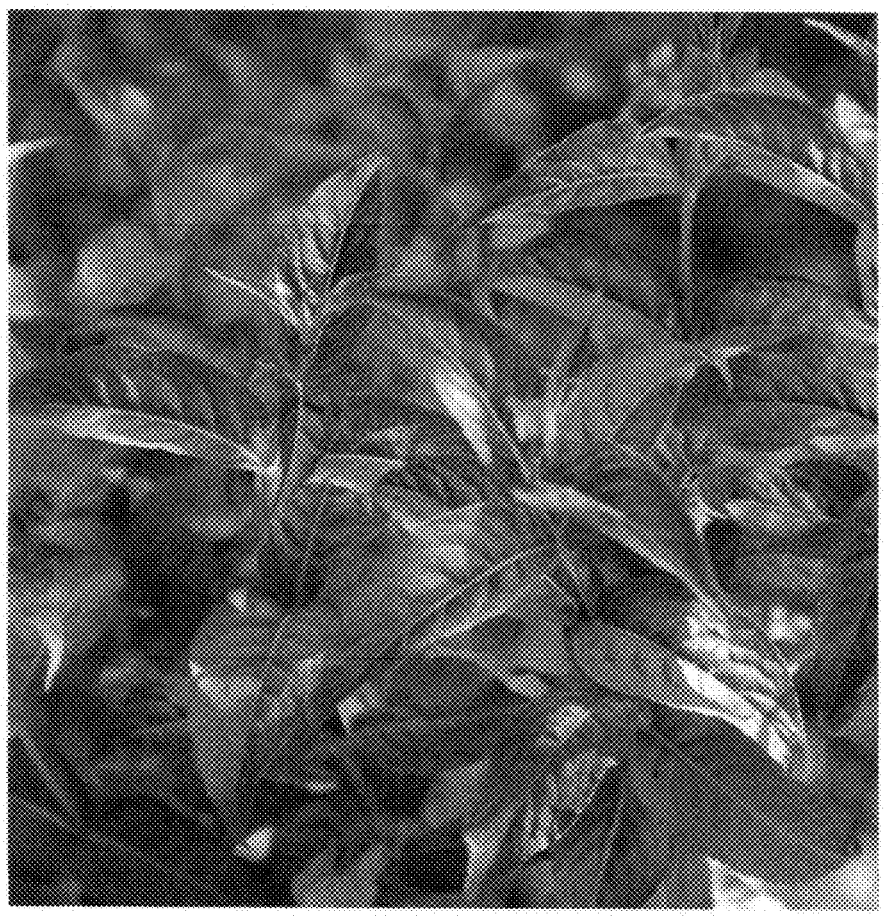

* * * * *